(12) United States Patent
Deterre et al.

(10) Patent No.: US 9,014,818 B2
(45) Date of Patent: Apr. 21, 2015

(54) ENERGY HARVESTER DEVICE FOR AUTONOMOUS INTRACORPOREAL CAPSULE

(75) Inventors: Martin Deterre, Paris (FR); Elie Lefeuvre, Montreuil (FR)

(73) Assignee: Sorin CRM SAS, Clamart (FR)

( * ) Notice: Subject to any disclaimer, the term of this patent is extended or adjusted under 35 U.S.C. 154(b) by 0 days.

(21) Appl. No.: 13/464,795

(22) Filed: May 4, 2012

(65) Prior Publication Data
US 2012/0283807 A1    Nov. 8, 2012

(30) Foreign Application Priority Data

May 4, 2011    (FR) ..................... 11 53790

(51) Int. Cl.
*A61N 1/378*    (2006.01)
*A61N 1/375*    (2006.01)

(52) U.S. Cl.
CPC .............. *A61N 1/3785* (2013.01); *A61N 1/3756* (2013.01)

(58) Field of Classification Search
USPC ........................ 607/33, 60, 61, 116
See application file for complete search history.

(56) References Cited

U.S. PATENT DOCUMENTS

| | | | |
|---|---|---|---|
| 3,456,134 A | 7/1969 | Ko | |
| 6,088,215 A * | 7/2000 | Webb et al. | 361/306.3 |
| 7,610,092 B2 * | 10/2009 | Cowan et al. | 607/33 |
| 7,894,904 B2 * | 2/2011 | Cowan et al. | 607/45 |
| 7,965,016 B2 | 6/2011 | Despesse et al. | |
| 7,996,087 B2 * | 8/2011 | Cowan et al. | 607/33 |
| 2005/0256549 A1 | 11/2005 | Holzer | |
| 2006/0136004 A1 | 6/2006 | Cowan et al. | |
| 2006/0217776 A1 | 9/2006 | White et al. | |
| 2007/0088397 A1 | 4/2007 | Jacobson | |
| 2007/0167988 A1 | 7/2007 | Cernasov | |
| 2007/0276444 A1 | 11/2007 | Gelbart et al. | |

(Continued)

FOREIGN PATENT DOCUMENTS

| | | |
|---|---|---|
| FR | 2896635 A1 | 7/2007 |
| GB | 2350302 A | 11/2000 |

(Continued)

OTHER PUBLICATIONS

Foreign Search Report (Annexe Au Rapport De Recherche Preliminaire Relatif A La Demande De Brevet Francais No. FR 1153790 FA 751723), Dec. 20, 2011.
F. Peano et al., *Design and Optimization of a MEMS Electret-Based Capacitive Energy Scavenger*, Journal of Microelectromechanical Systems, 14 (3), 429-435, Jun. 2005.

(Continued)

*Primary Examiner* — Niketa Patel
*Assistant Examiner* — Christopher A Flory
(74) *Attorney, Agent, or Firm* — Foley & Lardner LLP (57) ABSTRACT

A method for powering an autonomous intracorporeal leadless capsule includes the step of receiving a slow pressure variation at an external surface of a deformable member on the capsule. The deformable member is displacing in response to the slow pressure variation. The method further includes using a high pass mechanical filter to prevent the displacement from being transferred to an energy harvesting circuit within the capsule. The method further includes receiving a fast pressure variation at the external surface of the deformable member on the capsule, the deformable member displacing in response to the fast pressure variation. The method further includes via the high pass mechanical filter, passing the displacement to the energy harvesting circuit and creating energy using the displacement provided to the energy harvesting circuit.

12 Claims, 6 Drawing Sheets

(56) References Cited

U.S. PATENT DOCUMENTS

| | | | |
|---|---|---|---|
| 2008/0262562 A1 | 10/2008 | Roberts et al. | |
| 2009/0021292 A1 | 1/2009 | Yu et al. | |
| 2009/0216292 A1 | 8/2009 | Pless et al. | |
| 2009/0240299 A1 | 9/2009 | Adekore et al. | |
| 2010/0160994 A1 | 6/2010 | Feldman et al. | |
| 2011/0190849 A1* | 8/2011 | Faltys et al. | 607/50 |
| 2012/0078322 A1* | 3/2012 | Dal Molin et al. | 607/32 |
| 2012/0093245 A1* | 4/2012 | Makdissi et al. | 375/259 |
| 2012/0263218 A1* | 10/2012 | Dal Molin et al. | 375/224 |
| 2012/0283807 A1* | 11/2012 | Deterre et al. | 607/116 |

FOREIGN PATENT DOCUMENTS

| | | | |
|---|---|---|---|
| WO | WO 2007/047681 A2 | 4/2007 | |
| WO | WO 2007/149462 A2 | 12/2007 | |

OTHER PUBLICATIONS

S. Meninger et al., *Vibration-to-Electric Energy Conversion*, IEEE Transactions on Very Large Scale Integration (VLSI) Systems, vol. 9, No. 1 pp. 64-76, Feb. 2001.

M. Khbeis et al., *Design of a Hybrid Ambient Low Frequency, Low Intensity Vibration Energy Scavenger*, The Sixth International Workshop on Micro and Nanotechnology for Power generation and Energy Conversion Applications, Berkeley, 2006.

Y. Sakane et al., *The Development of a High-Performance Perfluorinated Polymer Electret and its Application to Micro Power Generation*, Journal of Micromechanics and Microengineering, vol. 18. pp. 1-6, Sep. 29, 2008.

E. Torres et al., *Electrostatic Energy-Harvesting and Battery-Charging CMOS System Prototype*, IEEE Transactions on Circuits and Systems I: Regular Papers, vol. 56, No. 9, 1938-1948, Sep. 2009.

* cited by examiner

ENERGY HARVESTER DEVICE FOR AUTONOMOUS INTRACORPOREAL CAPSULE

RELATED APPLICATIONS

This application claims the benefit of French Application No. 11/53790 entitled "Energy Harvester Device For Autonomous Intracorporeal Capsule" and filed May 4, 2011, which is hereby incorporated by reference in its entirety.

FIELD

The present invention relates to the field of "medical devices" as defined by the Jun. 14, 1993 directive 93/42/CE of the European Communities, and more particularly to the "active implantable medical devices" as defined by the of Jun. 20, 1990 directive 90/385/CEE of the European Communities. Such devices in particular include implantable medical devices that continuously monitor a patient's cardiac rhythm and deliver if necessary to the heart electrical pulses for cardiac stimulation, resynchronization, cardioversion and/or defibrillation in case of a rhythm disorder detected by the device. Such devices also include neurological devices, cochlear implants, etc., as well as devices for pH measurement or devices for intracorporeal impedance measurement (such as the measure of the transpulmonary impedance or of the intracardiac impedance). The invention relates even more particularly to those devices that implement autonomous implanted capsules and are free from any physical connection to a main implanted device (for example, the can of a stimulation pulse generator)

BACKGROUND

Autonomous implanted capsules are referred to as "leadless capsules" to distinguish them from the electrodes or sensors placed at the distal end of a lead, which lead is traversed throughout its length by one or more electrical conductors connecting by galvanic conduction the electrode or the sensor to a generator connected at the opposite, proximal end, of the lead.

Such leadless capsules are, for example, described in U.S. Patent Pub. No. 2007/0088397 A1 and WO 2007/047681 A2 (Nanostim, Inc.) and U.S. Patent Pub. No. 2006/0136004 A1 (EBR Systems, Inc.).

These leadless capsules can be epicardial capsules, which are typically fixed to the outer wall of the heart, or endocardial capsules, which are typically fixed to the inside wall of a ventricular or atrial cavity, by means of a protruding anchoring helical screw, axially extending from the body of the capsule and designed to penetrate the heart tissue by screwing to the implantation site.

In one embodiment, a leadless capsule includes detection/stimulation circuitry to collect depolarization potentials of the myocardium and/or to apply pacing pulses to the site where the leadless capsule is located. The leadless capsule then includes an appropriate electrode, which can be included in an active part of the anchoring screw.

It can also incorporate one or more sensors for locally measuring the value of a parameter such as the oxygen level in the blood, the endocardial cardiac pressure, the acceleration of the heart wall, the acceleration of the patient as an indicator of activity, etc. Of course, the leadless capsules incorporate transmitter/receiver means for wireless communication, for the remote exchange of data.

The present invention is nevertheless not limited to a particular type of leadless capsule, and is equally applicable to any type of leadless capsule, regardless of its functional purpose.

Whatever the technique implemented, the signal processing inside the leadless capsule and the remote transmission of data into or out of the leadless capsule requires a non negligible energy supply as compared to the energy resources a leadless capsule can store. However, due to its autonomous nature, the leadless capsule can only use its own resources, such as an energy harvester circuit (responsive to the movement of the leadless capsule), associated with an integrated small buffer battery. The management of the available energy is thus a crucial point for the development of autonomous leadless capsules and their capabilities, especially their ability to have an integrated self-power supply system.

Various techniques of energy harvesting have been proposed, adapted to leadless autonomous implants. U.S. Patent Pub. No. 2006/0217776 A1, U.S. Pat. No. 3,456,134 A and WO 2007/149462 A2 describe systems using piezoelectric transducers directly transforming into electrical energy the movement of a mass resulting from the acceleration of the patient's organs or body. However, given the relatively low excitation frequencies (below 10 Hz), the excursions of the movements are relatively large, which does not allow a for significant miniaturization. In addition, since these excitations do not have stable specific frequencies, the piezoelectric generator cannot operate in a resonant mode, and thereby loses much of its effectiveness.

Other devices have been proposed to transform pressure changes occurring within the body into electricity, including changes in blood pressure or those resulting from the movements of the patient's diaphragm during breathing. This transformation is effected by means of a magnetic microgenerator, functioning as an alternator or as a dynamo, by variations in magnetic flux induced in a coil. Reference is made to U.S. Patent Pub. No. 2005/0256549 A1, GB 2350302 A, U.S. Patent Pub. Nos. 2008/0262562 A1 and 2007/0276444 A1. Due to the presence of moving parts, however, the complexity of the design of the mechanical and electrical parts and their relatively large volume effectively limit, the miniaturization and the overall reliability of such a generator. Moreover and most importantly, such a generator is inherently sensitive to external magnetic fields and is not compatible with the magnetic resonance imaging systems (MRI) because of the very high static magnetic fields generated by these systems, typically in the order of 0.5 to 3 T or more.

It also has been proposed to use an electrostatic transducer made of electrodes modeling a capacitor, for example, with a set of combs and interdigitated-counter combs. One of the electrodes is secured to a support fixed on the body of the case, the other being coupled to an oscillating mass called "seismic mass". This mass is set in motion by movement of the entire system including the transducer, and it carries with it one of the electrodes of the transducer, which thus move relative to the other by a variation of the dielectric gap and/or of the facing surfaces of the two electrodes. If the capacitor is initially pre-loaded with an energy charge, or if the structure includes electrets (or electrets films) to maintain a continuous load, the capacity variation causes an energy increase in this capacitor that can be extracted by an electronic circuit and then stored in a buffer battery. The mechanical energy collected by the oscillating mass can thus almost entirely be converted into electrical energy in a single cycle. This technique is described, for example, by F. Peano and T. Tambosso, *Design and Optimization of a MEMS Electret-Based Capacitive Energy Scavenger*, Journal of Microelectromechanical Systems, 14 (3), 429-435, 2005, or S. Meninger et al. *Vibration-to-Electric Energy Conversion*, IEEE Transactions on Very Large Scale Integration (VLSI) Systems, vol. 9, no. 1, pp. 64-76, 2001. This type of transducer has the same drawbacks, however, as the piezoelectric transducers because of limitations imposed by the oscillating mass, both in terms of miniaturization (the seismic mass is relatively large) and efficiency with respect to the driving movements. Indeed, the relatively low excitation frequencies (below 10 Hz) involve relatively large excursions and/or a relatively high mass of the oscillating element, which does not allow a significant miniaturization.

Another known energy harvester system, without an oscillating weight, is disclosed by U.S. Patent Pub. No. 2009/021292A1. This document discloses an energy harvesting power system incorporated into an implantable capsule in which the housing body has a deformable element resulting from changes in pressure of the surrounding environment. The deformation of this element is transmitted to an electrostatic transducer directly converting the mechanical energy of deformation into electrical energy, which is then delivered to a power management and storage module powering the device with energy. Note that such a system does not need to be resonant or to contain magnetic elements. However, the system described utilizes pressure variations that result at least partly from mechanical forces applied to the capsule, under the effect of contact forces with the surrounding tissues or deformation thereof. Thus, in the case of a system that is fully submerged in a body fluid (for example such an energy harvesting system used in an intracardiac capsule blood pressure changes during rapid changes in the systole-diastole cycle), the slow variations of atmospheric pressure disrupt the operation of the energy harvesting system: indeed, as the capsule is strictly waterproof, its interior volume is initially at the pressure defined during manufacturing and the equilibrium point at rest of the deformable element is offset compared to the nominal rest position if the atmospheric pressure varies.

OBJECT AND SUMMARY

It is therefore an object of the present invention is to provide an improved power generator for an implantable autonomous leadless capsule.

It is another object to provide an energy harvesting circuit that ensures that changes in a patient's systole-diastole cardiac cycle are fully transmitted to the electrodes around the same nominal rest point.

Broadly, the present invention relates to an autonomous intracorporeal leadless capsule of a type similar to that described in the aforementioned U.S. Patent Pub. No. 2009/021292 A1, including a body and, within the body, electronic circuits and a power supply including:

an energy harvester transducer, for converting an external physical stress applied to the capsule to an electrical quantity, this transducer comprising:
- a first capacitor electrode, coupled with a movable actuator receiving said external physical stress, the movable element of actuation of the transducer being substantially free of an oscillating weight and comprising a deformable surface, formed on the exterior of the capsule body and being alternately deformed in one direction and in the other under the effect of pressure variations in the surroundings of the capsule; and
- a second capacitor electrode, mounted on a support connected to a region of the body other than the movable actuator, the two electrodes having facing surfaces separated by a dielectric gap together defining a capacitor (C), and said physical stress producing a consequential modification of said facing surfaces and/or of said dielectric gap with correlative variation of the capacity of said capacitor; and a storage and power management circuit, powered by the energy harvester transducer as a result of a decrease of the distance between the facing surfaces and/or of an increase the dielectric gap of the capacitor.

Both electrodes have facing surfaces separated by a dielectric together defining a capacitor, and the deformation of the deformable surface produces a corresponding modification of said facing surfaces and/or of said dielectric gap with correlative variation of the capacity of the capacitor. In addition, the management module includes a means for preloading a charge on the capacitor when its capacity is maximum, and of unloading the capacitor by transferring its energy changes to a storage device when this capacity decreases as a result of a decrease of the distance between the facing surfaces and/or of an increase of the dielectric gap of the capacitor.

Preferably, the deformable surface is coupled to the first electrode with the interposition of a damping element forming a mechanical high-pass filter with respect to pressure variations in the medium surrounding the capsule.

In one embodiment, the deformable surface has a rigid surface coupled to the first electrode and an elastically deformable structure, such as a bellows or other organ, for connecting the rigid surface to the body, or to a membrane coupled to the first electrode in a region of greater deformation of the latter.

In one embodiment, the first and second capacitor electrodes are advantageously made in the form of combs and interdigitated counter-combs, and the first capacitor electrode can be coupled to the body of the capsule by an elastically deformable support forming a guiding spring.

The leadless capsule may further comprise means for preloading the capacitor when its capacity is maximum, and for unloading it by transferring its stored energy to a storage device, e.g., a suitable battery or other device, when that capacity decreases as a result of a decrease in space between the facing surfaces and/or of an increase in the dielectric gap of the capacitor.

Advantageously, the present invention provides for improved miniaturization: compatibility with the extremely small volume (a few cubic millimeters) of a leadless implant;

Advantageously, the present invention provides for improved reliability: guaranteed secured operation over several years of lifetime of the implant;

Advantageously, the present invention provides for improved insensitivity to magnetic phenomena, including MRI compatibility which is now required for implanted devices.

Advantageously, the present invention provides for improved biocompatibility: absence of external elements that can cause inflammatory reactions.

DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements, and in which.

DETAILED DESCRIPTION

With reference to the drawing FIGS. 1-17, various examples of preferred embodiments of an electrostatically energy harvesting capsule will be described.

Figure 1:
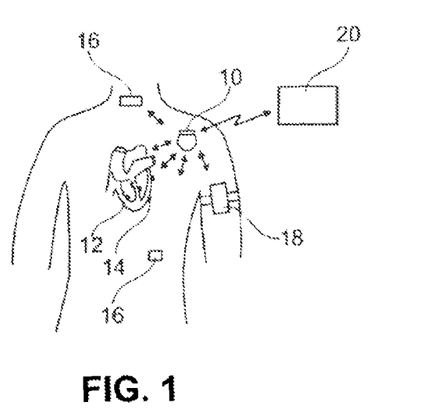
FIG. 1 schematically illustrates a set of medical devices including leadless capsules, implanted within the body of a patient.

With reference to FIG. 1, a set of medical devices implanted in the body of a patient is shown. This set is equipped with a device 10 such as an implantable defibrillator/pacemaker/resynchronizer, a subcutaneous defibrillator or a long-term recorder. Device 10 is deemed the master device of a network comprising a plurality of slave devices 12 to 18, which may include intracardiac 12 or epicardial 14 leadless capsules located directly on the patient's heart, other devices 16 such as myopotential sensors or neurological stimulation devices, and optionally an external device 18 disposed on armlets and provided with electrodes in galvanic contact with the skin.

Main device 10 also can be used as a gateway to the outside world to communicate via telemetry with a compatible external device 20 such as a programmer or a device for remote transmission of data.

Figure 2:
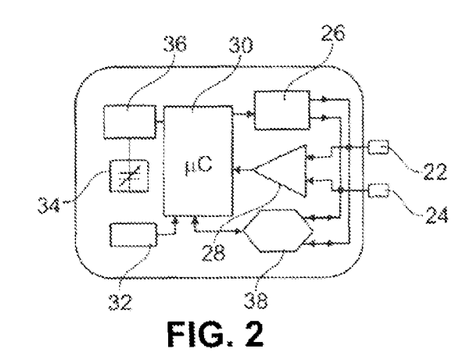
FIG. 2 is a functional block diagram showing the various components of a leadless capsule.

With reference to FIG. 2, an internal circuit of the implanted autonomous leadless capsules 12 to 16 is illustrated. The leadless capsule contains, for example, a pair of electrodes 22, 24 connected to a pacing pulse generator circuit 26 (e.g., for an active leadless capsule incorporating this function) and/or a detection circuit 28 for the collection of depolarization potentials collected between the electrodes 22 and 24. A central circuit 30 includes all the electronic required to control the various functions of the capsule, the storage the collected signals, etc. It comprises a microcontroller and an oscillator generating the clock signals needed for the operation of the microcontroller and for the communication. It may also contain an analog/digital converter and a digital storage memory. The capsule may also be provided with a sensor 32 such as, for example, an acceleration sensor, a pressure sensor, a hemodynamic sensor, a temperature sensor, and an oxygen saturation sensor. The leadless capsule also include an energy harvester circuit 34 powering all circuits via an energy management circuit 36. The electrodes 22 and 24 are also connected to a pulse transmission/reception circuit 38 used for wireless communication with the master device or the other leadless capsules.

The present invention more particularly relates to the energy harvester circuit 34 which, typically, uses the pressure variations of the surrounding environment, including the cyclic variations of blood pressure, to move an electrode of a capacitor element relatively to another electrode positioned vis-à-vis (i.e., facing) one another. The energy harvesting is obtained by the variation of capacity of the capacitor resulting from the relative displacement of the two electrodes, which causes a change in the spacing between their facing surfaces and/or a variation of the dielectric gap that separates them.

Figure 3:
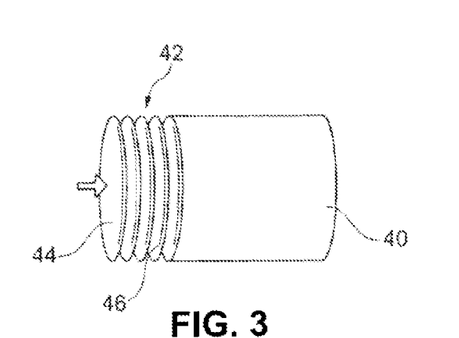
FIGS. 3 and 4 illustrate respectively two embodiments of a body of leadless capsule of the present invention.
Figure 4:
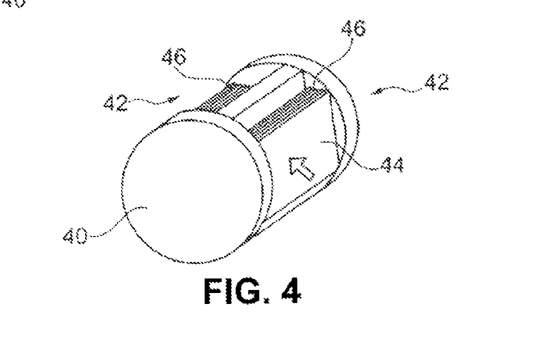

To take into account these deformations, preferably the capsule is provided in the form of a body 40, as shown in FIGS. 3 and 4, with one or more deformable elements 42 operating at the rhythm caused by the changes in the pressure of the fluid in which the capsule is immersed (typically, the variations of blood pressure, in the case of a cardiac capsule). Deformable element 42 includes a rigid surface 44 which is effected by the pressure exerted, and is connected to rest of the body by a deformable bellows 46, which moves in response to the effect of the external forces to which rigid surface 44 is exposed.

With reference to the embodiment illustrated in FIG. 3, this surface/bellows assembly 44, 46 is disposed on an axial end face of the capsule 40, which has a generally cylindrical shape. Dimensions are typically about 6 mm in diameter for a length of 20 mm, and provides a very small volume of about 0.5 cm$^3$.

With reference to the embodiment illustrated in the FIG. 4, two deformable sets 42 are arranged on side faces of the body 40 of the leadless capsule. Rigid surfaces 44 are connected to block 40 by bellows 46, with surfaces 44 arranged parallel to each other and to the main axis of the capsule. In this embodiment the energy harvesting system is split; it also frees the two axial ends of the capsule, which can be important, particularly to place an anchoring screw system with no obstacles to this configuration due to the energy harvesting system.

In one embodiment, the body 40 and its deformable element 42 are advantageously made in a monobloc form, for example, of evaporated titanium or electrodeposited on a soluble stylet.

Figure 5A:
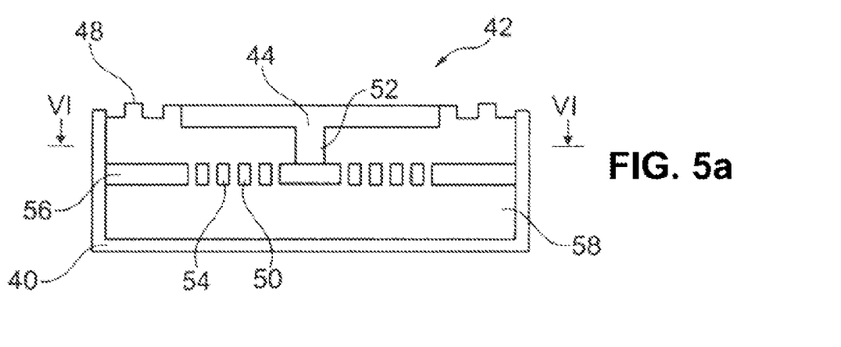
FIGS. 5a and 5b are schematic sectional views of a first embodiment of an electrostatically energy harvesting leadless capsule of the present invention.
Figure 5B:
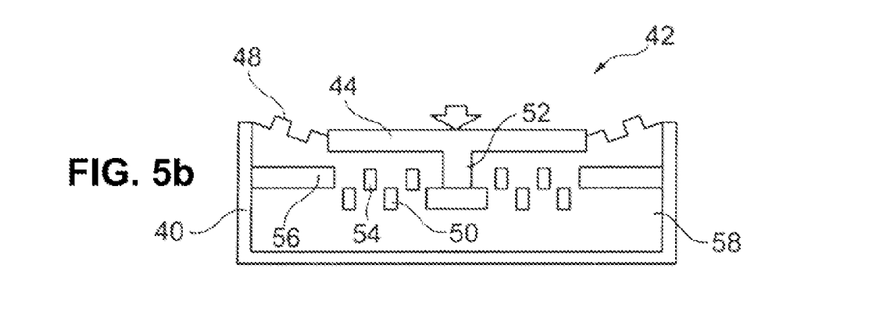
Figure 6:
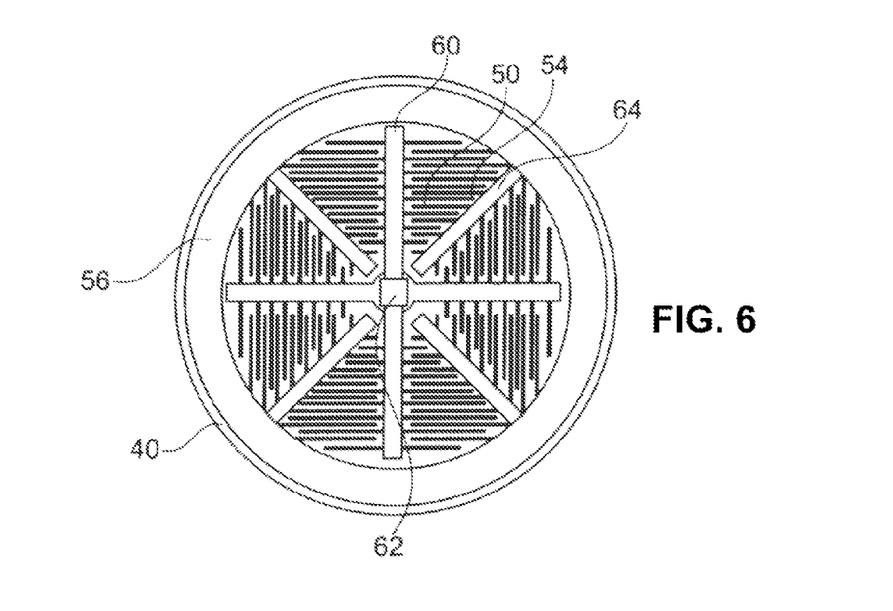
FIG. 6 is a plan view taken along line VI-VI of FIG. 5a, of the first embodiment of the electrostatically energy harvesting leadless capsule.

With reference to FIGS. 5a, 5b and 6, a first embodiment of an electrostatically energy harvesting capsule will be described here to illustrate the principle of the electrostatic transducer with variable capacitor.

In this first embodiment, deformable element 42 includes a planar rigid surface 44 coupled to body 40 of the capsule by an elastic element 48, preferably formed of peripheral ripples around rigid surface 44. Rigid surface 44, which is movable under the effects of the pressure variations of the surrounding environment, is connected to a series of first capacitor electrodes 50 via the coupling element 52, which is simply shown here a rod. As can be seen particularly in FIG. 4, electrodes 50 are preferably configured in the form of combs made, for example, by conventional photogravure (photolithography). The device also comprises second electrodes 54, for example, made in the form of counter-combs interdigitated with the combs of electrodes 50 (cf. FIG. 6), connected to the body 40 by a peripheral support 56. The assembly formed by electrodes 50, 54 is enclosed in a sealed volume 58 formed by body 40 closed by deformable member 42.

This provides a transducer that can be modelled by a variable capacitor comprising:

A first suspended electrode, incorporated by the combs 50 which are mechanically and electrically gathered by arms 60 and central support 62 connected to movable surface 44;

A second fixed electrode, constituted by the counter-combs 54 mechanically and electrically gathered together by the fixed arms 64 themselves attached to the body 40 via the annular support 56; and A dielectric gap, defined between the two electrodes.

With the combs and the interdigitated counter-combs, as illustrated FIG. 6, in the case of a depression of deformable element 42, the air gap and the overlap in the plane of the combs remain constant, but the vertical overlap changes during the movement. The capacity is maximum when the two structures (combs and counter-combs) are vertically at the same level, and is minimal (close to zero) when the movable structure (suspended combs 50) have moved by a distance equal to their thickness (as shown in FIG. 5b), having thus rendered almost null the facing surfaces of the combs with the counter-combs.

Concretely, when external pressure is exerted on movable surface 44, for example, during the systole in the case of a leadless capsule immersed in a blood medium, the pressure variation produces a depression of surface 44 towards the inside the leadless capsule, as shown in FIG. 5b. Combs 50 of the movable electrode then move away from fixed combs 54 of the fixed capacitor electrode and produce a variation in the capacity of the capacitor, in this case a decrease in that capacity because of the decrease of the facing surfaces of the stationary and movable electrodes and of the increase in the dielectric gap between these surfaces.

If the capacitor had previously been preloaded, the decrease in the capacity of the capacitor produces an energy excess which may be discharged by appropriate circuits to a storage device, and thus allows, at each systolic cycle, to recover an amount of energy that is eventually sufficient to ensure continuous operation of the electronic circuits of the leadless capsule without any additional energy contribution.

The preload of the capacitor can be performed by specific circuits, described below with reference to FIGS. 7-9.

In one embodiment, the preload can be achieved by annexed piezoelectric elements, which during the initial pressure variations deform and generate a voltage precharging the capacitor during its start-up, according to a technique notably described by Khbeis & al., *Design of a Hybrid Ambient Low Frequency, Low Intensity Vibration Energy Scavenger*, the Sixth International Workshop on Micro and Nanotechnology for Power Generation and Energy Conversion Applications, Berkeley, 2006, or in FR 2896635 A1.

In yet another embodiment, the preload can be avoided by having an electret structure on one side of the capacitor, these electrets generating the required electric field. This particular technique is described in the cited article Peano Tambosso discussed above, or by Sakane & al., *The Development of a High-Performance Perfluorinated Polymer Electret and Its Application to Micro Power Generation*, Journal of Micromechanics and Microengineering, Vol. 18, pp. 1-6, 2008.

Figure 7:
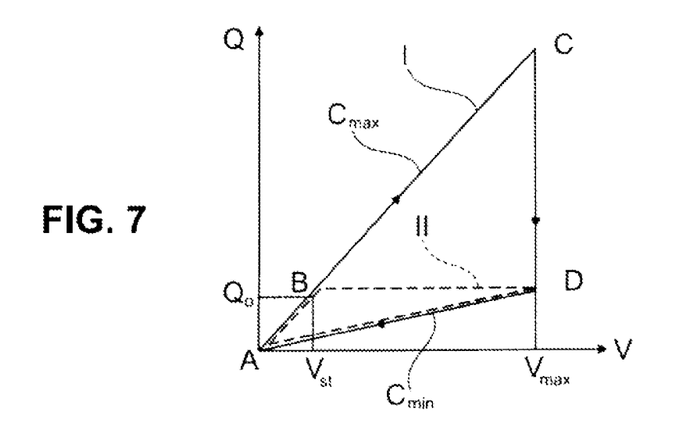
FIG. 7 is a load/voltage diagram illustrating two methods to operate the energy harvesting circuit, at constant load or at constant voltage, respectively.
Figure 8:
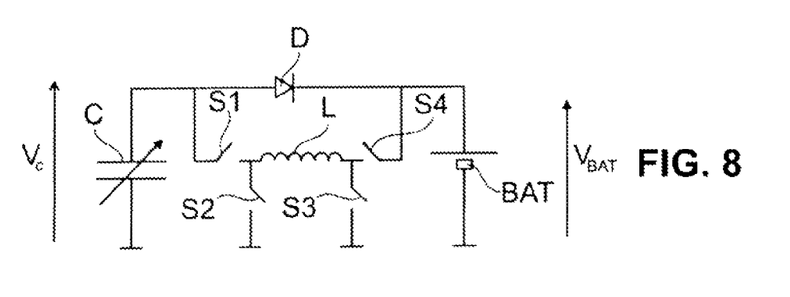
FIG. 8 is a schematic representation of an energy harvester circuit with constant voltage.
Figure 9:
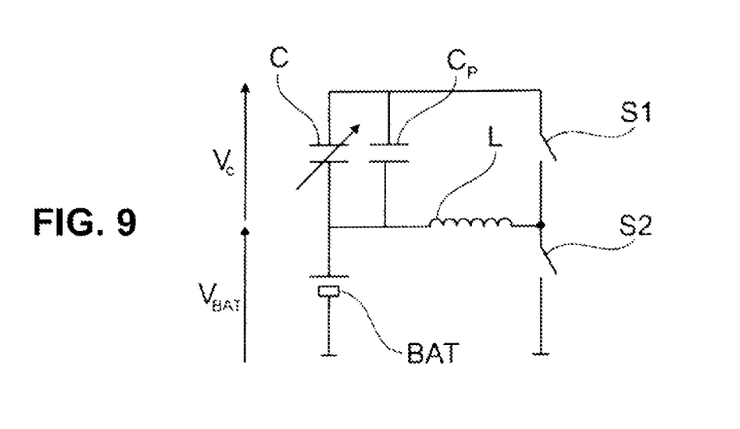
FIG. 9 is a schematic representation of an energy harvester circuit at constant load.

With reference to FIGS. 7-9, an embodiment of a method to harvest the energy through the change in the capacity of the capacitor is illustrated. Two techniques for recovery, respectively at constant voltage and constant load, will now be described. The diagram in FIG. 7 illustrates two charge/voltage characteristics for a full charge/discharge cycle of the variable capacitor. The characteristic I corresponds to a cycle following the path ACDA at constant voltage. The capacitor is initially charged to the maximum voltage $V_{max}$ (segment AC), while the capacity is maximum ($C=C_{max}$). This load is operated in a sufficiently short time (typically less than a microsecond) for this capacity to be considered constant. During the movement of the movable element, the capacity is reduced from $C_{max}$ to $C_{min}$, the voltage being held constant (by hypothesis) and maintained at Vmax, the characteristic follows the segment CD.

During this phase, the energy stored in the capacitor is transferred to the storage device. The residual charge $Q_0$ is then harvested by following the DA segment, with $C=C_{min}$. The total harvested energy is the area of the cycle I, $\frac{1}{2}(C_{max}-C_{min})V_{max}^2$.

In the case of a conversion at constant load (characteristic II following the path ABDA), the capacitor is initially charged to a starting voltage $V_{st}$, with a maximum capacity $C=C_{max}$ (segment AB).

The circuit is then left open (constant load $Q_0$) during the movement of the electrodes of the capacitor, which decreases the capacity from its maximum value $C_{max}$ to its minimum value $C_{min}$ (segment BD), the voltage increasing to its maximum value Vmax for satisfying the equation Q=CV. The bad is then returned (segment AD), in the same method as before. The total harvested energy is equal to the area of the cycle II, $\frac{1}{2}(C_{max}-C_{min})V_{st}V_{max}$. This value is, for the same maximum voltage $V_{max}$, lower than that of the solution at constant voltage (characteristic I); however, this solution may provide additional benefits, including the ability to operate with a low initial voltage. It is also possible to provide an additional capacitor, connected in parallel with the variable capacitor C, to increase the energy and thus reach closer performance to the solution at constant voltage.

FIG. 8 schematically illustrates an exemplary circuit for energy harvesting at constant voltage. This circuit configuration is in itself known, and for details one can refer, for example, to E. Torres and G. Rincon-Mora, Electrostatic *Energy-Harvesting and Battery-Charging CMOS System Prototype*, IEEE Transactions on Circuits and Systems I: Regular Papers, Vol. 56, No. 9, 1938-1948, September 2009.

Essentially, the four switches 51 to S4 are initially open and the circuit monitors the voltage across the capacitor C for detecting when it becomes maximum. At that moment, the preload phase is triggered, starting first of all by loading the inductance L (S1 and S3 closed, S2 and S4 open), then by discharging this inductance L in the capacitor C (S1 and S3 open, S2 and S4 closed), all in a very short time with respect to the variation of capacity of the capacitor C. The switches are then opened, and the diode D fixes the voltage across C, by discharging the capacitor into a storage device, preferably a battery BAT, thus loading it.

FIG. 9 illustrates a circuit diagram of an energy harvesting circuit at constant load. This circuit is also known, and more details can be found in the aforementioned article of S. Meninger et al. *Vibration-to-Electric Energy Conversion*, IEEE Transactions on Very Large Scale Integration (VLSI) Systems, vol. 9, no. 1, p. 64-76, 2001.

Essentially, the voltage across the capacitors C and Cp (an additional capacitor Cp is optionally added in parallel to C to increase the produced energy) is initially zero. When the control circuit detects the maximum capacity of the capacitor C, S1 opens and S2 closes, loading the inductance L, then immediately after S1 closes and S2 opens, which transfers energy from L to capacitors C and Cp. Then the two switches S1 and S2 open and the capacity of capacitor C declines as a result of mechanical forces, to the minimum value $C_{min}$. At that moment, S1 is closed and S2 remains open, which loads the inductance L from the energy accumulated in the capacitors C and Cp. As soon as the voltage at the terminations of the latter is equal to zero, S1 opens and S2 closes, which allows transferring the collected energy from the inductor L to the storage device, preferably battery BAT.

Figure 10:
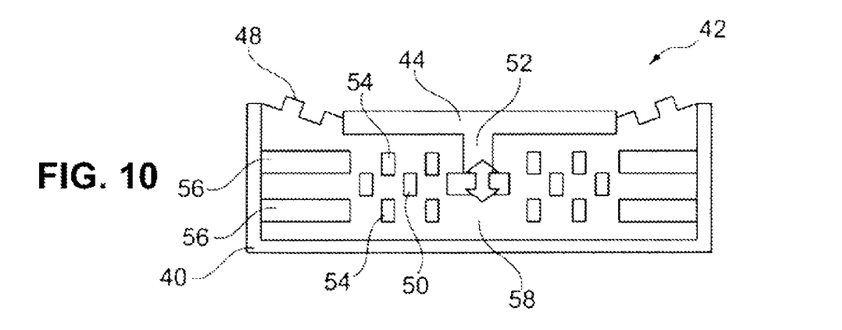
FIG. 10 illustrates a second embodiment of an electrostatically energy harvesting leadless capsule of the present invention, for energy harvesting in both directions of movement of the movable electrode.

FIG. 10 illustrates a second embodiment of an electrostatically energy harvesting leadless capsule, wherein the electrode formed by the movable comb 50 is, at rest, positioned between two fixed superimposed counter-combs 54, so that the movable comb 50 comes next to one or the other of the counter-combs 54 along the direction of movement of the membrane. This allows harvesting the energy when the membrane moves in either direction, for example, during both phases of systole and diastole in the case wherein the leadless capsule is surrounded by a blood medium.

Figure 11:
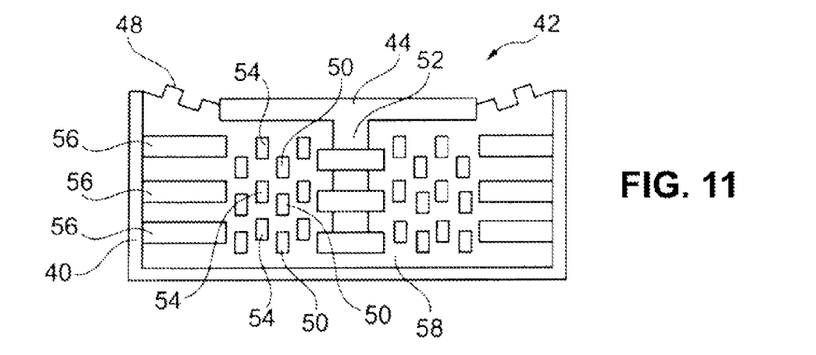
FIG. 11 illustrates a third embodiment of an electrostatically energy harvesting leadless capsule, of the present invention using a stack of structures such as that illustrated in FIG. 5a for the first embodiment.

FIG. 11 illustrates a third embodiment of an electrostatically energy harvesting leadless capsule, wherein the transducer is a multilayer structure as described with reference to FIGS. 5 and 6, to increase the electrode surface by the further multiplication of the combs/counter-combs sets, which maximizes the difference between minimum capacity $C_{min}$ and maximum capacity $C_{max}$.

Figure 12:
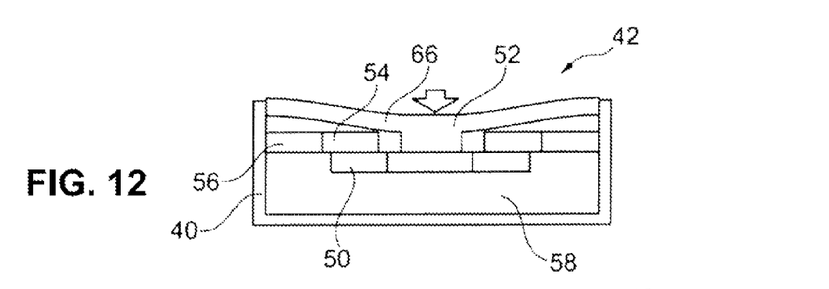
FIG. 12 illustrates a fourth embodiment of an electrostatically energy harvesting leadless capsule, wherein the deformable element is a flexible membrane.

FIG. 12 illustrates a fourth embodiment of an electrostatically energy harvesting leadless capsule, wherein deformable element 42 is made of a flexible membrane 66, fixed to housing 40 of the leadless capsule at its periphery and bearing in its center the part 52 for connection to movable electrode 50.

Figure 13:
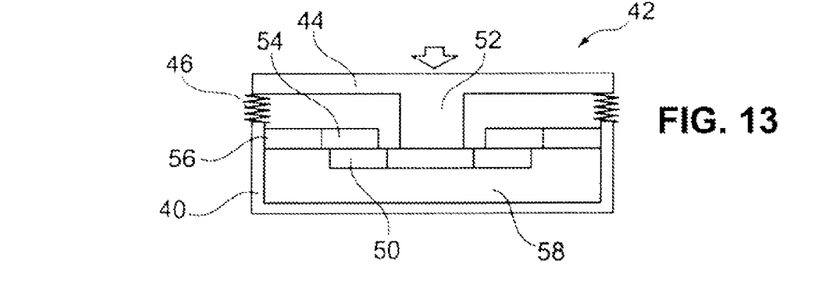
FIG. 13 illustrates a fifth embodiment of an electrostatically energy harvesting leadless capsule, using a bellows for connecting the movable element to the body of the capsule.

FIG. 13 illustrates a fifth embodiment of an electrostatically energy harvesting leadless capsule, wherein deformable element 42 is made of a rigid movable element 44 extending from one edge to the other of housing 40, connected to housing 40 by an elastic element 46 in the form of bellows instead of peripheral ripples 48 as illustrated in the embodiments of FIGS. 10 and 11. This configuration advantageously allows in particular increasing both the travel of movable member 44, and therefore that of the movable electrode, and the surface of rigid movable member 44 over which the external pressure is applied, with correlative increase of the force exerted at the center of this element.

Figure 14:
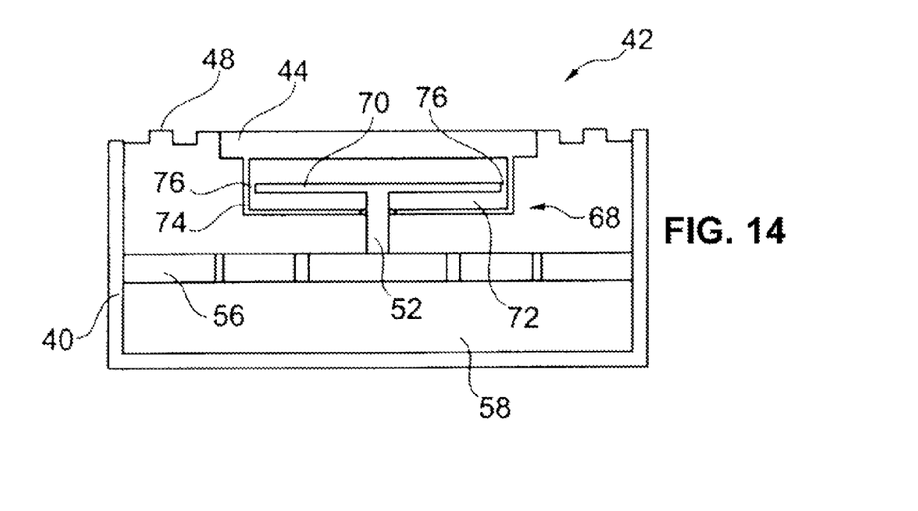
FIG. 14 illustrates an embodiment of a leadless capsule according to the present invention, applicable to the various embodiments described above, that eliminate the effects of the slow variations of pressure.

FIG. 14 shows an improvement of the present invention, which is equally applicable to the various embodiments described above. This embodiment is configured to overcome one of the problems of harvesting of the forces exerted by changes in blood pressure, which is the change in atmospheric pressure. Indeed, the inside of the leadless capsule is sealed and therefore strictly at constant pressure (adjusted at the factory during manufacture). If the atmospheric pressure varies, the equilibrium at rest of the deformable element is offset relative to the nominal position at rest.

The proposed solution of the embodiment illustrated in FIG. 14 is to replace the rigid coupling between deformable element 42 and the movable electrode by a coupling incorporating a mechanical high-pass filter 68 interposed between the deformable element submitted to the external pressure and the electrostatic movable structure. This filter, for example, includes a piston 70 having a rod 52 connected to the movable electrode, with piston 70 moving in a fluid 72 such as air or other gas enclosed in a sealed enclosure 74. In this way, the slow movements of deformable member 42 due to changes in atmospheric pressure are not transferred to the suspended movable electrode, the fluid being able to flow from either side of piston 70 through, by example, microstructured holes, or by a calibrated clearance 76, so as to restore the pressure equilibrium. However, during rapid changes in the systole-diastole cardiac cycle, these pressure changes are fully transmitted to the suspended electrode, which can fully play the role assigned to it.

Figure 15:
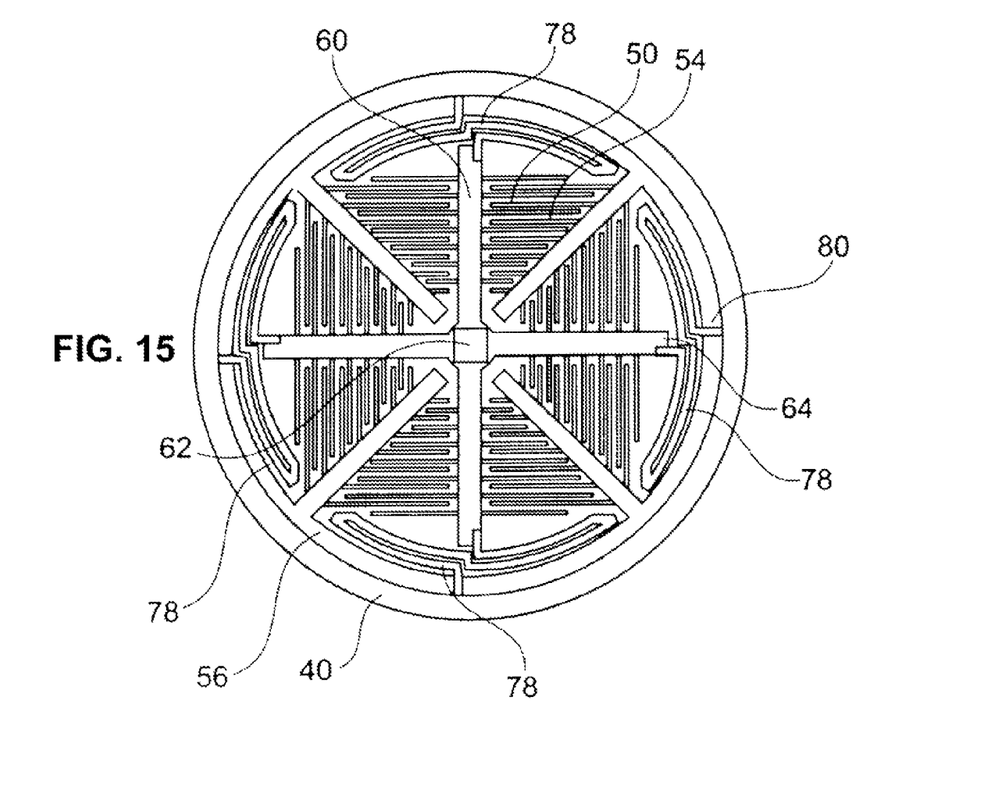
FIG. 15 illustrates an embodiment of an electrostatically energy harvesting leadless capsule, using photolithographic technology to produce fixed combs and movable counter-combs suspended by guiding springs.

FIG. 15 illustrates an embodiment in the monolithic form of the structure combs/counter-combs produced by conventional photolithography techniques. Indeed, one of the difficulties of designing interdigitated structures of combs and counter-combs is to obtain a dielectric gap as small as possible, to maximize the capacity, while maintaining sufficient tolerance to prevent the combs to come in contact, to avoid they are unstable under the influence of the implemented electrostatic forces if the transverse stiffness of the fingers is too low, and that a breakdown between the electrodes happens if the electric field is too intense.

The device presented in the various embodiments described above (which are not in themselves limited), with a variable overlap out of plane, advantageously allows realization by conventional, in themselves known, microfabrication to manufacture electrostatic comb devices.

The combs 50 and counter-combs 54 can thus be simultaneously manufactured on a single slice of a typical substrate of silicon, heavily doped to be conductive. The separation of the combs to form the dielectric gap can be realized by deep etching of silicon using a technique such as DRIE (Deep Reactive Ion Etching), allowing for example to obtain gaps of less than 10 microns on a slice thickness of the order of 300 to 500 microns. With gaps as low as 10 µm, for the gap between the combs remains constant and to avoid that the latter do not come to contact, alignment and assembly of two independent structures of combs is difficult. To overcome this difficulty, the structure can be performed on a slice of SOI (Silicon On Insulator) the substrate of which is structured so as to form, as shown in FIG. 15, the combs and counter-combs 50, 54 and their common supporting elements 60, 64, and wherein the upper layer (active) of the slice is structured so as to form very broad and thin springs 78 between each of the supports 64 of the movable structure and the peripheral ring 80 connected to the body 40 of the capsule.

These springs, because of their configuration, present an important rigidity in the plane containing the suspended movable structure of the combs 50, and greatly limit the transverse displacements, typically at less than 1 µm. These elements ensure therefore, in addition a function of elastic support in the axial direction, a guiding and centering function in the transverse plane, thus guaranteeing a substantially constant dielectric gap. Because of the very small thickness of the springs 78, they are very flexible in the vertical direction (axial), which therefore allows deformable member 42 of the leadless capsule and the suspended electrode constituted of combs 50 to axially move without difficulty and without adding significant stiffness.

Figure 16:
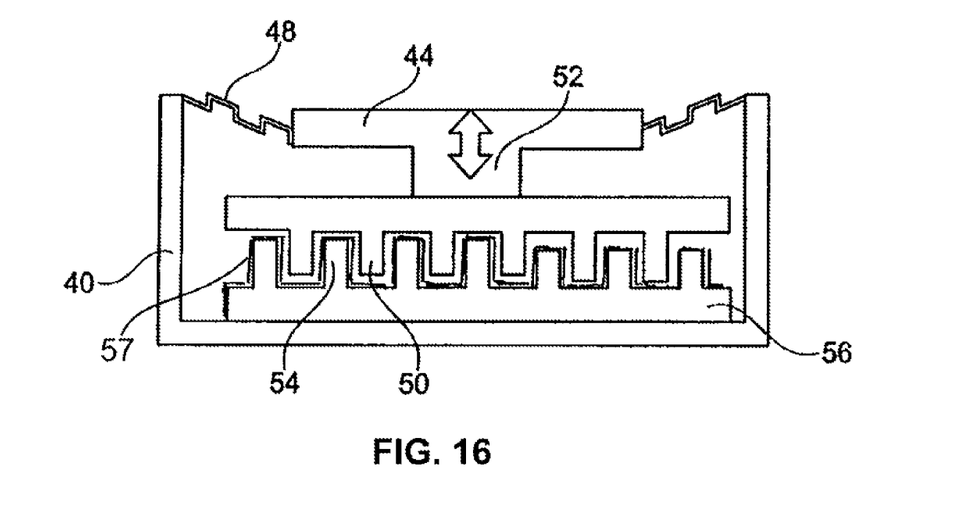
FIGS. 16 and 17 illustrate two alternative embodiments of the capacitor structure, particularly adapted to the use of armatures carrying electrets.
Figure 17:
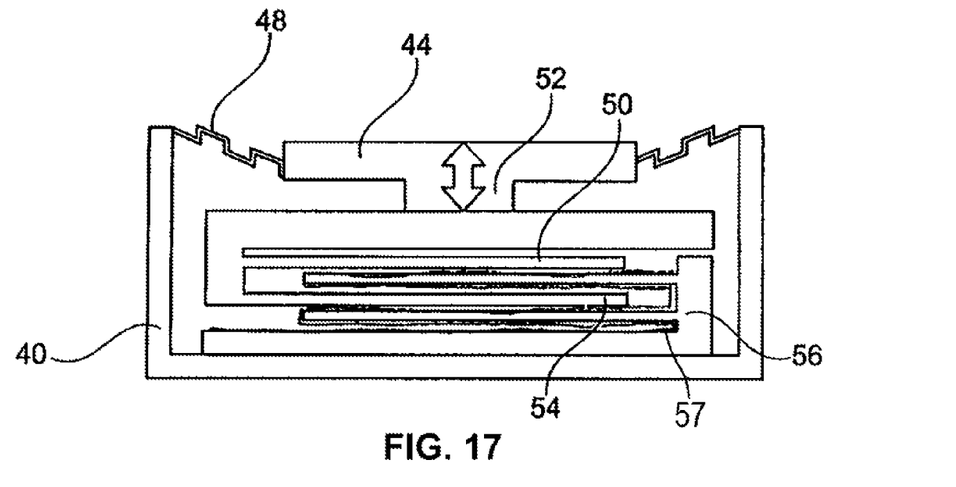

FIGS. 16 and 17 illustrate two alternative embodiments of the capacitor structure, adapted to the use of reinforcement electret armatures having an electret film 57, as described in the aforementioned articles of Peano & al. and Sakane & al. In this case, the electrodes are advantageously configured with overlap in the plane (FIG. 16) or with a variable dielectric gap (FIG. 17). The rest of the structure of the transducer is iden-

The invention claimed is:

1. An autonomous intracorporeal leadless capsule, comprising:
   a capsule body having an exterior and an interior;
   an electronic circuit disposed in said interior and an energy harvesting circuit disposed in said interior;
   a transducer for energy harvesting, for converting an external physical effect applied to the capsule body into an electrical charge, the transducer comprising:
   (a) a first capacitor electrode, coupled to a movable actuation member receiving said external physical effect, said movable actuation member actuation being substantially free of an oscillating weight and comprising a deformable surface, on the exterior of the body, said deformable surface being deformed in a first direction and a second direction opposite said first direction in response to an effect of pressure variations in a medium surrounding the body, and
   (b) a second capacitor electrode, mounted on a support connected to a region of the body other than the movable actuation member, the first and second capacitor electrodes having respective surfaces separated by a dielectric gap together defining a capacitor, and said pressure variation, producing a correlative modification of said surfaces and/or of said dielectric gap with correlative variation of the capacity of said capacitor; and
   an energy storage and management circuit, powered by the energy harvester transducer in response to a reduction and/or an increase of the dielectric gap of the capacitor, wherein said deformable surface is coupled to the first capacitor electrode by a mechanical high-pass filter,
   wherein the mechanical high-pass filter comprises a piston having a rod coupled to at least one moveable surface of the capacitor, wherein the piston is enclosed within a fluid-filled chamber that is fixed to and moveable with the deformable surface with respect to at least the capsule body and piston, the rod extending from the piston out of the fluid-filled chamber to the at least one moveable surface of the capacitor, wherein the spaces within the fluid-filled chamber above and below the piston are coupled via a calibrated clearance between the piston and inner surface of the fluid-filled chamber sized to restore pressure equilibrium during slow movements of the deformable surface but to transmit pressure changes to the piston, the rod, and the movable surface of the capacitor, and wherein displacement of the piston is not caused during low frequency displacement of the deformable member.

2. The capsule of claim 1, wherein the deformable surface further comprises a rigid surface coupled to the first capacitor electrode and an elastically deformable member connecting said rigid surface to said body.

3. The capsule of claim 1, wherein the deformable surface further comprises a flexible membrane coupled to the first capacitor electrode having a region of greater deformation.

4. The capsule of claim 1, wherein the first and second capacitor electrodes are constructed in the form of interdigitated combs and counter-combs.

5. The capsule of claim 1, wherein the first capacitor electrode is coupled to the body by an elastically deformable support forming a guiding spring.

6. The capsule of claim 1, further comprising means for preloading the capacitor when its capacity is maximum, and for discharging said capacitor by transferring its energy to the storage circuit when said capacity decreases under the effect of a reduction in surfaces in and/or of an increase of the dielectric gap of the capacitor.

7. The capsule of claim 1, wherein at least of the first the second capacitor electrodes comprises an electret film.

8. An autonomous intracorporeal leadless capsule, comprising:
   a circuit;
   an energy harvesting device with at least one moveable surface for powering the circuit;
   a capsule body having a deformable element directly exposed to the environment exterior of the capsule body, the circuit and the energy harvesting device within the capsule body;
   a mechanical high-pass filter positioned within the capsule body, wherein the mechanical high-pass filter comprises a piston having a rod coupled to at least one moveable surface of the energy harvesting device, wherein the piston is enclosed within a fluid-filled chamber that is fixed to and moveable with the deformable element with respect to at least the capsule body and piston, the rod extending from the piston out of the fluid-filled chamber to the at least one moveable surface of the energy harvesting device, wherein the spaces within the fluid-filled chamber above and below the piston are coupled via a calibrated clearance between the piston and inner surface of the fluid-filled chamber sized to restore pressure equilibrium during slow movements of the deformable element but to transmit pressure changes to the piston, the rod, and the movable surface of the capacitor so as to allow the deformable element to move with slow movements but to prevent the slow movements from being transferred to the energy harvesting device, wherein the mechanical high pass filter allows rapid movements to be transmitted to the energy harvesting device.

9. The capsule of claim 8, wherein the energy harvesting device comprises:
   a capacitor fully within the capsule body and not directly exposed to the environment exterior of the capsule body, the capacitor comprising opposing capacitor electrodes separated by a dielectric gap, the dielectric gap together with the opposing capacitor electrodes forming the capacitor, wherein the opposing capacitor electrodes are movably suspended relative to the capsule body such that relative movement of the opposing capacitor electrodes creates power for providing to the circuit, wherein the mechanical high-pass filter mechanically decouples the deformable element and the movable capacitor electrodes during slow movements of the deformable element.

10. The capsule of claim 9, wherein the mechanical high-pass filter comprises a piston coupled to at least one movable surface of the capacitor, wherein displacement of the piston is not caused during low frequency displacement of the deformable member.

11. The capsule of claim 10, wherein the piston is enclosed within a fluid-filled chamber movable with the deformable member.

12. The capsule of claim 11, wherein the spaces within the fluid-filled chamber above and below the piston are coupled via a hole sized to restore pressure equilibrium during slow movements of the deformable member but to transmit pressure changes to the piston and the movable surface of the capacitor.

* * * * *